United States Patent [19]

Loesch-Fries et al.

[11] Patent Number: 5,736,627
[45] Date of Patent: Apr. 7, 1998

[54] VIRUS RESISTANT PLANTS HAVING COAT PROTEIN

[75] Inventors: L. Sue Loesch-Fries, Shorewood Hills; Nancy P. Jarvis; Donald J. Merlo, both of Madison, all of Wis.

[73] Assignee: Pioneer Hi-Bred International, Inc., Johnston, Iowa

[21] Appl. No.: 174,829

[22] Filed: Mar. 29, 1988

Related U.S. Application Data

[63] Continuation-in-part of Ser. No. 847,434, Apr. 2, 1986, abandoned.

[51] Int. Cl.[6] .............................. A01H 5/00; C12N 15/40; C12N 15/82; C12N 15/84
[52] U.S. Cl. ................. 800/205; 800/250; 800/DIG. 24; 536/23.72; 435/69.1; 435/172.3; 435/252.2; 435/252.3; 435/252.33; 435/320.1; 435/418; 435/419
[58] Field of Search ...................... 435/320, 69.1, 435/172.3, 252.2, 252.3, 252.33, 320.1, 418, 419; 536/27, 23.72; 800/1, 205, 250, DIG. 24

[56] References Cited

U.S. PATENT DOCUMENTS

| | | | |
|---|---|---|---|
| 4,407,956 | 10/1983 | Howell | 435/172.3 |
| 4,536,475 | 8/1985 | Anderson | 435/172.3 |

FOREIGN PATENT DOCUMENTS

| | | |
|---|---|---|
| 0 120 516 | 10/1984 | European Pat. Off. |
| 0 223 452 | 5/1987 | European Pat. Off. |
| WO 84/02913 | 8/1984 | WIPO |

OTHER PUBLICATIONS

Abel, P.P. et al., "Delay of Disease Development in Transgenic Plants that Express the Tobacco Mosaic Virus Coat Protein Gene," *Science* 232:738–743 (May 1986).
Barker, R.F. et al., "Complete nucleotide sequence of alfalfa mosaic virus RNA3," *Nucl. Acids Res.* 11(9):2881–2891 (1983).
Beachy, R.N. et al., "Potential for Applying Genetic Transformation to Studies of Viral Pathogenesis and Cross-Pollination," in: *Biotechnology in Plant Science—Relevance to Agriculture in the Eighties*, Zaitlin, M. et al., eds., Academic Press, Inc., San Diego, CA, pp. 265–275 (1985).
Beachy, R.N. et al., "Virus Genes Might Protect Plants from Disease," *Genet. Technol. News* 5(8):4–5 (Aug. 1985).
Bevan, M., "Binary *Agrobacterium* vectors for plant transformation," *Nucl. Acids Res.* 12(22):8711–8721 (1984).
Bevan, M.W. et al., "Expression of tobacco mosaic virus coat protein by a cauliflower mosaic virus promoter in plants transformed by *Agrobacterium*," *EMBO J.* 4(8):1921–1926 (1985).
Bialy, H. and A. Klausner, "A New Route to Virus Resistance in Plants," *Bio/Technol.* 4:96 (Feb. 1986).
Brederode, F.T. et al., "Complete nucleotide sequence of alfalfa mosaic virus 4," *Nucl. Acids Res.* 8(10):2213–2223 (1980).
Brisson, N. et al., "Expression of a bacterial gene in plants by using a viral vector," *Nature* 310:511–514 (1984).

Freeman, K., "Monsanto Creates TMV Resistant Plants," *Genet. Eng. News* 6(2):18 (Feb. 1986).
Fulton, R.W., "The Protective Effects of Systemic Virus Infection," in: *Active Defense Mechanisms in Plants*, Wood, R.K.S., ed., Plenum Press, New York, pp. 231–245 (1982).
Goodman, R.M. et al., "Gene Transfer in Crop Improvement," *Science* 236:48–54 (Apr. 1987).
Gould, A.R. and R.H. Symons, "Alfalfa Mosaic Virus RNA. Determination of the Sequence Homology Between the Four RNA Species and a Comparison with the Four RNA Species of Cucumber Mosaic Virus," *Eur. J. Biochem.* 91:269–278 (1978).
Hepburn, A.G. and J. White, "The Effect of Right Terminal Repeat Deletion on the Oncogenicity of the T-Region of PTIT-37," *Plant. Mol. Biol.* 5(1):3–12 (1985).
Horsch, R.B. et al., "Inheritance of Functional Foreign Genes in Plants," *Science* 223:496–498 (1984).
Houwing, C.J. and E.M.J. Jaspars, "Coat Protein Binds to the 3'-Terminal Part to RNA 4 of Alfalfa Mosaic Virus," *Biochem.* 17(14):2927–2933 (1978).
Klee, H.J. et al., "Vectors for Transformation of Higher Plants," *Bio/Technol.* 3:637–642 (1985).
Koper-Zwarthoff, E.C. et al., "Nucleotide sequence of the 3'-noncoding region of alfalfa mosaic virus RNA 4 and its homology with the genomic RNAs," *Nucl. Acids Res.* 7(7):1887–1900 (1979).
Koziel, M.G. et al., "A Cauliflower Mosaic Virus Promoter Directs Expression of Kanamycin Resistance in Morphogenic Transformed Plant Cells," *J. Mol. Appl. Genet.* 2(6):549–562 (1984).
Loesch-Fries, L.S. et al., "Cloning of alfalfa-mosaic virus coat protein gene and anti-sense RNA into a binary vector and their expression in transformed tobacco tissue," *J. Cell. Biochem. Suppl.* 10c: Abstract No. 41 (1986).
Rubin, R.A., "Genetic Studies on the Role of Octopine T DNA Border Regions in Crown Gall Tumor Formation," *Mol. Gen. Genet.* 202(2):312–320 (1986).
Schmelzer, K., "Untersuchungen an Viren der Zier–und Wildgehölze. 1. Mitteilung Virosen an *Viburnum* und *Ribes*," *Phytopathol. Z.* 46:17–52 (1963).
Sequeira, L., "Cross protection and induced resistance: their potential for plant disease control," *Trends Biotechnol.* 2(2):25–29 (1984).
Shaw, C.H. et al., "The right hand copy of the nopaline Ti-plasmid 25 bp repeat is required for tumor formation," *Nucl. Acids Res.* 12(15):6031–6041 (1984).
Sherwood, J.L. and R.W. Fulton, "Specific Involvement of Coat Protein in Tobacco Mosaic Virus Cross Protection," *Virol.* 119(1):150–158 (1982).
Toyoda et al. 1983. Ann. Phytopath. Soc. Japan 49: 639–646.

*Primary Examiner*—David T. Fox
*Attorney, Agent, or Firm*—Sterne, Kessler, Goldstein & Fox, PLLC

[57] ABSTRACT

The making of plant cells which contain coat protein of a target plant virus is disclosed. Construction of coat protein genes and transformation of coat protein genes into plant cells is also taught. Such cells are relatively resistant to infection by the target virus when compared with cells not containing coat protein. Furthermore, methods and DNA molecules useful for producing plant cells containing coat protein are also disclosed.

25 Claims, No Drawings

VIRUS RESISTANT PLANTS HAVING COAT PROTEIN

This is a continuation-in-part of U.S. patent application Ser. No. 847,434, filed Apr. 2, 1986, now abandoned, which is incorporated herein by reference.

FIELD OF THE INVENTION

The present invention is in the fields of genetic engineering and plant husbandry, and especially provides a means for producing a virus resistant plant by transforming a plant to contain a plant-expressible foreign gene directing synthesis of a viral coat protein. Also provided are plant-transforming prokaryotic plasmid vectors carrying such plant-expressible RNA and plant cells transformed by such a vector.

BACKGROUND OF THE INVENTION

Overview of Agrobacterium

Virulent strains of the gram-negative genus Agrobacterium harbor large plasmids known as Ti (tumor- or transformation-inducing) plasmids (pTi) in *A. tumefaciens* and Ri (root-inducing) plasmids (pRi) in *A. rhizogenes*, often classified by the opine which they catabolize or cause to be synthesized. Ti and Ri plasmids both contain DNA sequences, known as T-DNA (transferred-DNA), which in tumors are found to be integrated into the genome of the host plant. Several T-DNA genes are under control of T-DNA promoters which resemble canonical eukaryotic promoters in structure. These plasmids also carry genes outside the T-DNA region. Ti and Ri plasmids are for many purposes functionally equivalent.

Reviews of Agrobacterium-caused disease, plant transformation, genetic engineering, and gene expression include those by, or found in Merlo, D. J. (1982) Adv. Plant Pathol. 1:139–178; Ream, L. W. and Gordon, M. P. (1982) Science 218:854–859; Bevan, M. W. and Chilton, M.-D. (1982) Ann. Rev. Genet. 16:357–384; Kahl, G. and Schell, J. (1982) Molecular Biology of Plant Tumors; Barton, K. A. and Chilton, M.-D. (1983) Methods Enzymol. 101:527–539; Depicker, A. et al. (1983) in *Genetic Engineering of Plants: an Agricultural Perspective*, Kosuge, T. et al. (eds.), pp. 143–176; Caplan, A. et al. (1983) Science 222:815–821; Hall, T. C. et al. European patent application no. 126,546; Binns, A. N. (1984) Oxford Surveys Plant Mol. Cell Biol. 1:130–160; Hall, T. C. (1985) Oxford Surveys Plant Mol. Biol. 2:329–338; Hooykaas, P. J. J. and Schilperoort, R. A. (1985) Trends Biochem. Sci. 10:307–309; Thomas, T. L. and Hall, T. C. (1985) Bioassays 3:149–153; Weissbach, A. and Weissbach H. (eds.) (1986) Methods Enzymol. 118 (see especially Rogers, S. G. et al. pp. 627–640); Puhler, A. (ed.) (1983) Molecular Genetics of the Bacteria-Plant Interaction; and Schilperoort, R. A. (1984) in *Efficiency in Plant Breeding* (Proc. 10th Congr. Eur. Assoc. Res. Plant Breeding), Lange, W. et al. (eds.), pp. 251–285.

Transformation of Plants by Agrobacterium

Plant cells can be transformed by Agrobacterium by several methods well-known in the art. For a review of recent work, see Syono, K. (1984) Oxford Surveys Plant Mol. Cell Biol. 1:217–219.

The infection of plant tissue by Agrobacterium is a simple technique well-known to those skilled in the art. Typically after being wounded, a plant is inoculated with a suspension of the bacteria. Alternatively, tissue pieces are inoculated, e.g. leaf disks (Horsch, R. B. et al. (1985) Science 227:1229–1231). After induction with wild-type Agrobacterium, the tumors are capable of phytohormone-independent growth. Traditional inoculation and culture techniques may be modified for use of disarmed T-DNA vectors incapable of hormone-independent growth (e.g. see Zambryski, P. et al. (1984) in Genetic Engineering, Principles, and Methods 6, Hollaender, A. and Setlow, J. (eds.), pp. 253–278).

Agrobacterium is also capable of infecting isolated cells, cells grown in culture, callus cells, and isolated protoplasts (e.g. Fraley, R. T. et al. (1984) Plant Mol. Biol. 3:371–378; Fraley, R. T. and Horsch, R. B. (1983) in *Genetic Engineering of Plants: an Agricultural Perspective*, Kosuge, T. et al. (eds.), pp. 177–194; Muller, A. et al. (1983) Biochem. Biophys. Res. Comm. 123:458–462). The transformation frequency of inoculated callus pieces can be increased by addition of an opine or opine precursors (Cello, L. M. and Olsen, W. L., U.S. Pat. No. 4,459,355).

The host range of crown gall pathogenesis may be influenced by T-DNA-encoded functions such as onc genes (Hoekema, A. et al. (1984) J. Bacteriol. 158:383–385; Hoekema, A. et al. (1984) EMBO J. 3:3043–3047; Buchholz, W. C. and Thomasshow, M. F. (1984) 160:327–332; Yanofsky, M. (1985) Mol. Gen. Genet. 201:237–246). Vir genes also affect host range (Yanofsky, supra). Ausich, R. L., European Patent Application 108,580, reports transfer of T-DNA from *A. tumefaciens* to green algal cells, and expression therein of ocs and Tn5 kanamycin resistance genes. Hooykaas-van Slogteren, G. M. S. et al. (1984) Nature 311:763–764, and Hernalsteens, J.-P. et al. (1984) EMBO J. 3:3039–3041, have demonstrated transformation of monocot cells by Agrobacterium without the customary tumorigenesis.

T-DNA, disarmed T-DNA, and functional foreign genes of transformed plants are usually transmitted through meiosis to progeny seemingly unaltered in a dominant, closely-linked, Mendelian fashion (e.g. see Horsch, R. B. et al. (1984) Science 223:496–498; Tepfer, D. (1984) Cell 37:959–967; DeBlock, M. et al. (1984) EMBO J. 3:1681–1689; Wostemeyer, A. et al. (1984) Mol. Gen. Genet. 194:500–507; Wallroth, M. et al. (1986) Mol. Gen. Genet. 202:6–15). Two unlinked T-DNAs can transform a single cell and, after plant regeneration, segregate in the F1 generation (de Framond, A. J. et al. (1986) Mol. Gen. Genet. 202:125–131).

Ti Plasmid DNA

T-DNA is often integrated (i.e. inserted) into host DNA at multiple sites in the nucleus. Flanking plant DNA may be either repeated or low copy number sequences. Integrated T-DNA can be found in either direct or inverted tandem arrays and can be separated by spacers. T-DNA can also transform chloroplasts (De Block, M. et al. (1985) EMBO J. 4:1367–1372; see review by Flavell, R. B. (1985) Bioassays 3:177–178).

The complete sequence of the T-DNA of an octopine-type plasmid found in ATCC 15955, pti15955, has been reported (Barker, R. F. et al. (1983) Plant Mol. Biol. 2:335–350) as has the TL region of pTiAch5 (Gielen, J. et al. (1984) EMBO J. 3:835–846). Published T-DNA genes do not contain introns. Sequences resembling canonical eukaryotic promoter elements and polyadenylation sites can be recognized.

Octopine Ti plasmids carry an ocs gene which encodes octopine synthase (lysopine dehydrogenase). Koncz, C. et al. (1983) EMBO J. 2:1597–1603 provides a functional analysis of ocs. Dhaese, P. et al. (1983) EMBO J. 2:419–426, reported the utilization of various polyadenylation sites by "transcript 7" (ORF3 of Barker, R. et al. supra) and ocs. The presence of the enzyme octopine synthase within a tissue can protect that tissue from the toxic effect of various amino acid analogs, e.g. aminoethyl cysteine (Dahl, G. A. and Tempe, J. (1983) Theor. Appl. Genet. 66:233–239; Koziel, M. G. et al. (1984) J. Mol. Appl. Genet. 2:549–562).

Nopaline Ti plasmids encode the nopaline synthase gene (nos) (sequenced by Depicker, A. et al. (1982) J. Mol. Appl. Genet. 1:561–573). Shaw, C. H. et al. (1984) Nucl. Acids Res. 12:7831–7846, provides a functional analysis of nos. Genes equivalent to tms and tmr have been identified on a nopaline-type plasmid (Willmitzer, L. et al. (1983) Cell 32:1045–1056).

Ti and Ri plasmid genes outside of the T-DNA region include the vir genes, which when mutated result in an avirulent Ti plasmid. The vir genes function in trans, being capable of causing the transformation of plant cells with T-DNA of a different plasmid type and physically located on another plasmid. Such arrangements are known as binary systems and the T-DNA bearing plasmids are generally known as micro-Ti plasmids. Disclosed binary systems and micro-Ti plasmids include the following: Hoekema, A. et al. (1985) Plant Mol. Biol. 5:85–89; Deblaere, R. et al. (1985) Nucl. Acids Res. 13:4777–4788; van den Elzen, P. et al. (1985) Plant Mol. Biol. 5:149–154; Anderson, D. M., U.S. Pat. No. 4,536,475; de Framond, A. J. et al. (1983) Biotechnol. 1:262–269; Hoekema, A. et al. (1983) Nature 303:179–180; Hille, J. et al. (1984) J. Bacteriol. 158:754–756; Hoekema, A. et al. (1984) J. Bacteriol. 158:383–385; An, G. et al. (1985) EMBO J. 4:277–284; Anderson, D. M., U.S. Pat. No. 4,536,475; Klee, H. J. et al. (1985) Biotechnol. 3:637–642; de Framond, A. J. et al. (1986) Mol. Gen. Genet. 202:125–131; Dahl, G. A. et al., European patent application 140,556; and Bevan, M. (1984) Nucl. Acids Res. 12:8711–8721. T-DNA need not be on a plasmid to transform a plant cell; chromosomally located T-DNA is functional (Hoekema, A. et al. (1984) EMBO J. 3:2485–2490). T-DNA has direct repeats of about 25 base pairs associated with the left and right borders, i.e. with the T-DNA/plant DNA junctions, which may be involved in either transfer from Agrobacterium or integration into the host genome. Ti plasmid-determined characteristics have been reviewed by Merlo, supra (see especially Table II), and Ream and Gordon, supra.

Foreign Gene Expression

A gene encoding bean phaseolin has been transferred into and expressed in sunflower tumors (Murai, N. et al. (1983) Science 222:476–482). The phaseolin gene was expressed at a high level in developing tobacco seeds (Sengupta-Gopalan, C. et al. (1985) Proc. Natl. Acad. Sci. USA 82:3320–3324). Similar results have been observed with a homologous gene, soybean beta-conglycinin (Beachy, R. N. et al. (1985) EMBO J. 4:3047–3053). A gene for the endosperm protein zein, from the monocot Zea mays, is transcribed in sunflower callus (Matzke, M. A. et al. (1984) EMBO J. 2:1525–1531). Expression of a pea RuBP-Case small subunit gene is light-regulated in transformed petunia cells; the pea small subunit protein produced is correctly processed and sequestered within chloroplasts (Broglie, R. et al. (1984) Science 224:838–843). Sequences involved in this light-inducibility and those needed for maximal expression have been identified (Morelli, G. et al. (1985) Nature 315:200–204; Nagy, F. et al. (1985) EMBO J. 4:3063–3068; Timko, M. P. et al. (1985) Nature 318:579–582). Expression of a wheat chlorophyll a/b binding protein gene is light-regulated and organ-specific in transformed tobacco plants (Lamppa, G. et al. (1985) Nature 316:750–752). A soybean heat shock gene is thermoinducible in sunflower tissue (Schoffl, F. and Baumann, G. (1985) EMBO J. 4:1119–1124). (A Drosophila melanogaster heat shock promoter is similarly functional in tobacco tissue (Spena, A. et al. (1985) EMBO J. 4:2739–2743).

Chimeric Genes Having T-DNA Promoters

The nos promoter can drive expression of drug resistance structural genes useful for selection of transformed plant cells. Resistance genes have been created for kanamycin (Bevan, M. W. et al. (1983) Nature 304:184–187; Fraley, R. T. et al. (1983) Proc. Natl. Acad. Sci. USA 80:4803–4807; Herrera-Estrella, L. et al. (1983) EMBO J. 2:987–995), methotrexate (Herrera-Estrella, et al. supra), chloramphenicol (Herrera-Estrella, L. et al. (1983) Nature 303:209–213), hygromycin B (van den Elzen, P.J.M. et al. (1985) Plant Mol. Biol. 5:299–302). Helmer, G. et al. (1984) Biotechnol. 2:520–527, have created a fusion gene having the promoter and 5'-end of the structural gene of nos fused to E. coli beta-galactosidase (lacZ) sequences. Plant tissues transformed with this screenable marker may be recognized by a characteristic color when grown on the appropriate chromogenic substrate. Fusion protein genes between the ocs structural gene, which also provided promoters, and structural genes for hygromycin B resistance and phaseolin have been created and are functional (Waldron, C. et al. (1985) Plant Mol. Biol. 5:103–108; Murai, N. et al. (1983) Science 222:476–482). An ocs driven glyphosate gene has been constructed (Comai, L. et al. (1985) Nature 317:741–744).

Promoters for octopine TL genes ORF24 and ORF25 could also drive structural gene expression (Velten, J. et al. (1984) EMBO J. 3:2723–2730; Velten, J. and Schell, J. (1985) Nucl. Acids Res. 13:6981–6998; Gelvin, S. B. et al. (1985) Mol. Gen. Genet. 199:240–248; Comai, L. et al. (1985) Nature 317:741–744).

Chimeric Genes Having Plant Promoters

A chimeric RuBP-Case small subunit/kanamycin resistance protein was translocated into the chloroplast (Van den Broeck, G. et al. (1985) Nature 313:358–363). That gene's promoter confers light-inducible expression in callus to chloramphenicol and kanamycin resistance genes (Herrera-Estrella, L. et al. (1984) Nature 310:115–120; Facciotti, D. et al. (1985) Biotechnol. 3:241–246). A chalcone synthase promoter also drove light-inducible expression of a kanamycin resistance gene (Kaulen, H. et al. (1986) EMBO J. 5:1–8). Chlorophyll a/b binding protein promoters have been used to drive expression of ocs and kanamycin resistance structural gene (Jones, J. D. G. et al. (1985) EMBO J. 4:2411–2418; Simpson, J. et al. (1985) EMBO J. 4:2723–2729).

Chimeric Genes Having Viral Promoters

A kanamycin resistance gene under control of a cauliflower mosaic virus (CaMV) promoter was expressed in plant cells transformed by T-DNA (Koziel, M. G. et al. (1984) J. Mol. Appl. Genet. 2:549–562). A methotrexate resistance gene behind the CaMV 35S promoter conferred methotrexate resistance (Brisson, N. et al. (1984) Nature 310:511–514). Tobacco mosaic virus coat protein has been expressed in transformed tobacco tissue under control of a CaMV promoter (Bevan, M. W. et al. (1985) EMBO J. 4:1921–1926). Odell, J. T. et al. (1985) Nature 313:810–812, have mapped sequences of the CaMV 35S promoter needed for transcription.

Transformation of Plants without Agrobacterium

Direct transfer of DNA into plant cells has been recently reviewed (Jones, M. G. K. (1985) Nature 317:579–580; Potrykus, I. et al. (1985) Plant Mol. Biol. Rep. 3:117–128; Howe, C. (1985) Trends Genet. 1:38–39; Paszkowski, J. and Saul, M. W. (1986) Methods Enzymol. 118:659–668; Power, J. B. et al. (1986) Methods Enzymol. 218:578–594). Both dicot and monocot cells can be directly transformed by kanamycin-selectable markers under control of either a nos or CaMV promoter (Paszkowski, J. et al. (1984) EMBO J.

3:2717–2722; Gardner, R. C. et al. (1984) Plant Mol. Biol. Rep. 2:3–8; Hain, R. et al. (1985) Mol. Gen. Genet. 199:161–168; Potrykus, I. et al. (1985) Mol. Gen. Genet. 199:183–188; Lorz, H. et al. (1985) Mol. Gen. Genet. 199:178–182; Shillito, R. D. et al. (1985) Biotechnol. 3:1099–1103; Meyer, P. et al. (1985) Mol. Gen. Genet. 201:513–518). Distinct DNA molecules can be co-transformed into a plant cell; it is advantageous that one DNA in the mixture carries a selectable marker (Peerbolte, R. et al. (1985) Plant Mol. Biol. 5:235–246). Descendants of plants regenerated from such transformed cells inherit the transformed hybrid gene as a single, dominant, Mendelian trait (Potrykus, et al. Mol. Gen. Genet. Supra).

CaMV has proven useful as a plant transformation vector (Brisson, N. et al. (1984) Nature 310:511–514; Brisson, N. and Hohn, T. (1986) Methods Enzymol. 118:659–668). Bromegrass mosaic virus (BMV), an RNA virus, can also be used in plants to express foreign structural genes (French, R. et al. (1986) Science 231:1294–1297).

Electroporation has proven useful for introducing chimeric genes into plant cells in a transient expression system (Fromm, M. et al. (1985) Proc. Natl. Acad. Sci. USA 82:5824–5828) and for stable transformation of maize cells (Fromm, M. E. et al. (1986) Nature 319:791–793).

Cells can take up DNA surrounded by membranes. DNA, including pTi DNA, may be introduced via liposomes (e.g. Deshayes, A. et al. (1985) EMBO J. 4:2731–2737) or by fusion of plant and bacterial cells after removal of their respective cell walls (e.g. Hain, R. et al. (1984) Plant Cell Rep. 3:60–64). Plant protoplasts can take up cell wall delimited Agrobacterium cells. T-DNA can be transmitted to tissue regenerated from fused protoplasts.

DNA can be stably integrated into a plant genome after microinjection (Crossway, A. et al. (1986) Mol. Gen. Genet. 202:179–185).

Introduction of DNA into plant cells during fertilization or pollination has been reported for corn and cotton by Ohta, Y. (1986) Proc. Natl. Acad. Sci. USA 83:715–719, and Zhou, G.-Y., et al. (1983) Methods Enzymol. 101:433–481, respectively.

Overview of AMV

Alfalfa mosaic virus (AMV) is one of a class of plant viruses having a tripartite, single-stranded, plus-stranded RNA genome. The genome (excluding the subgenomic RNA molecules) is segmented into three RNA molecules. This class includes: the alfalfa mosaic virus (AMV) group, the ilarviruses, the bromoviruses, the cucumoviruses, and the hordei-viruses (van Vloten-Doting, L. et al. (1981) Intervirol. 15:198–203; Matthews, R. E. F. (1982) Classification and Nomenclature of Viruses). The genome segments are separately encapsidated in bacilliform particles of different lengths. Besides the three genomic RNA components (RNA1, RNA2, and RNA3), a fourth subgenomic RNA (RNA4) is found in virus preparations. A mixture of the three genome RNAs, together with a small amount of coat protein or its messenger RNA4 (Bol, J. F. et al. (1971) Virol. 46:73–85) is required to initiate infection.

The complete sequence of AMV RNA4 has been disclosed (Brederode, F. T. et al. (1980) Nucl. Acids Res. 8:2213–2223). RNA4 is 881 nucleotides in length. The coding region is 660 nucleotides (not including the initiation and termination codon) flanked by a 5'-untranslated region of 39 nucleotides and a 3'-untranslated region of 182 nucleotides. The sequence of RNA4 is present in and located at the 3'-end of RNA3 (Gould, A. R. and Symons, R. H. (1978) Eur. J. Biochem. 91:269–278).

The complete nucleotide sequence of AMV RNA3 has been disclosed (Barker, R. F. et al. (1983) Nucl. Acids Res. 11:2881–2891). A 240 base 5'-noncoding region precedes a 903 nucleotide open reading frame (ORF). This ORF is followed by a 49 base intercistronic region and a 666 nucleotide ORF, this latter ORF encoding AMV coat protein. The coat protein gene is followed by a 179 base 3'-untranslated sequence. AMV RNA4 is identical to and determined by the 3'-end of RNA3, having 36 nucleotides of the intercistronic region, the coat protein structural gene, and the 3'-untranslated sequence.

The complete nucleotide sequence of AMV RNA1 has been disclosed (Cornelissen, B. J. C. et al. (1983) Nucl. Acids Res. 11:1253–1265). RNA1 is 3645 nucleotides in length and it contains an ORF for a protein of Mr 125,685 flanked by a 5'-untranslated sequence of 99 nucleotides and a 3'- untranslated region of 163 nucleotides.

Comparison of the 3'-terminal sequences of all four AMV RNAs reveals extensive homology between the 3'-terminal 140 to 150 nucleotides (Houwing, C. J. and Jaspars, E. M. J. (1978) Biochem. 17:2927–2933). There are about 20 base substitutions in the 3'-terminal 145 nucleotides of the AMV RNAs but these are either located in the loops of base paired structures or convert A-U base pairs to G-C base pairs in the stems of the secondary structure hairpins (Koper-Zwarthoff, E. C. et al. (1979) Nucl. Acids Res. 7:1887–1900).

Cross Protection

Cross protection refers to a phenomenon wherein a plant infected by one strain of a virus is much less susceptible than an uninfected plant to superinfection by another strain of a related virus. Reviews of cross protection, induced systemic protection, and interaction of viruses during infection include Fulton, R. W. (1982) in Active Defense Mechanisms in Plants, Wood, R. K. S. (ed.), pp. 231–245; Ross, A. F. (1974) Acta Hort. 36:247–260; Dean, R. A. and Kuc, J. (1985) Trends Biotechnol. 125–129; and Sequeira, L. (1984) Trends Biotechnol. 2:25–29. Cross protection has been demonstrated for AMV (Schmelzer, K. (1963) Phytopathol. Z. 46:17–52; ("snowball mosaic virus" is a synonym for AMV)). The mechanism of cross protection can be explained by a number of hypotheses (see Ross supra; Fulton supra; and Sequeira supra). The mechanism need not be the same for all viruses (e.g. see Fulton supra, pp. 240–241). One hypothesis is that the presence of coat protein in a plant tissue interferes with establishment of an infection by a superinfecting virus (de Zoeten, G. A. and Fulton, R. W. (1975) Phytopathol. 65:221–222). However, the role of coat protein in cross protection has not been established. Evidence supporting this hypothesis for cross protection between tobacco mosaic virus (TMV) strains has been presented (Sherwood, J. L. and Fulton, R. W. (1982) Virol. 119:150–158). However, other evidence indicates that coat protein is not involved in TMV cross protection (Sarkar, S. and Smitamana, P. (1981) Mol. Gen. Genet. 184:158–159; Zaitlin, M. (1976) Phytopathol. 66:382–383). The mechanisms for cross protection of AMV strains and TMV strains may not be the same, as the role of coat protein in infection, the virion structures, and the natures of coat protein-coat protein interactions and coat protein-nucleic acid interactions, are different for these two viruses.

Plant cells infected by a virus naturally contain coat protein molecules that are not incorporated into virions. Sequeira supra, suggests that if TMV coat protein proves to be involved in inhibiting uncoating of superinfecting virions, it might be useful to use a T-DNA vector to introduce a plant-expressible coat protein gene. Bevan, M. W. et al. (1985) EMBO J. 4:1921–1926, used such a TMV coat protein gene/vector combination to transform tobacco cells. Though low levels of TMV coat protein were accumulated in the transformed callus tissues, protection from infection by TMV was not reported. Informal reports state that tobacco plants transformed by a similar vector/gene combination can be resistant to TMV infection (e.g. Bialy, H. and Klausher, A. (1986) Biotechnol. 4:96; Freeman, K. (1986) Genet. Eng. News 6(2):18).

SUMMARY OF THE INVENTION

This invention relates to the occurrence of viral infections in plants and to the efforts of horticulturists and agronomists to combat these infections in economically significant plant species. Virus infections occur in every known plant species and cause significant reductions in the yield and quality of all agricultural and horticultural plant species. The plant industry in no country in the world is exempt from such virally-caused damage and no consistent treatment is known to treat or prevent such viral infections. For example, 90% of the cassava plants in Kenya are infected by cassava mosaic virus resulting in an estimated 75% reduction in yield. As another example, in a recent viral epidemic in Ghana, more than one hundred million cacao trees were lost by infection with swollen shoot virus. Many other examples could be given making it evident that viral epidemics and infections have a vast economic significance. The reduction in yield from food crops is also relevant to the steadily increasing human population of the world and to the chronic malnutrition that already exists. Therefore, it is clear that both the means for creating virus-resistant plant genotypes and the resultant plants themselves would be very useful for increasing the world's ability to feed itself.

In particular, alfalfa mosaic virus has been shown to cause serious decreases in crop yield. AMV infects alfalfa and other annual legume crops. This is economically important; in the United States alone approximately 30 million acres are planted in alfalfa. Alfalfa mosaic virus also causes economically-important diseases in crop plants such as peppers, potatoes, celery, peas, and beans. Alfalfa can be an overwintering host from which aphids carry the virus. The disease is also spread from alfalfa to other species of crop plants following a build-up of aphid infestation. In many cases, plants infected by AMV show no symptoms making it difficult to detect the occurrence and spread of the disease. In other cases, the mosaic disease is evident but by that time the virus has almost certainly spread through a large area of plants in a field.

Apart from the removal of infected plants and the use of insecticides to kill the aphids which transmit the virus, there are no practical methods developed for preventing the spread of AMV. Therefore, it is clear that both the means for creating AMV-resistant genotypes and the resulting plants would be very useful for increasing agricultural productivity of a number of crops.

Therefore, it is an object of the present invention to provide plants having novel virus resistance genes and, in particular, to provide plants resistant to AMV infection. Toward this goal, methods for creating viral resistance genes, in particular, coat protein genes inhibitory of viral replication, are provided. Also provided are plants, plant cells, plant tissues, and plant seeds containing coat protein genes which are responsible for those plant materials having a viral resistance phenotype. Furthermore, DNA molecules useful for creating such virus resistant plants are also described. The present invention is exemplified by putting into tobacco a coat protein gene that is transcribed into a translatable alfalfa mosaic virus coat protein-encoding transcript.

In nature, plant cells do not contain viral coat protein unless they have been infected with that virus. Infected plants contain complete viral genomes in addition to coat protein. In general, plant cells have not been caused to contain coat protein without a viral infection. This is believed to be true in the case of AMV, though an exception to this statement might include plants transformed to contain plant-expressible TMV coat protein genes (see Cross Protection). As discussed in the Background section on Cross Protection, before the present disclosure it was uncertain whether coat protein was involved in preventing super-infection of plants. It was also uncertain whether all examples of cross protection were due to the same mechanism. In other words, it was uncertain whether protection, due to the presence of coat protein, of a plant from infection by one particular virus could be extrapolated to protection from infection by another, unrelated virus due to presence of its coat protein.

DETAILED DESCRIPTION OF THE INVENTION

The following definitions are provided, in order to remove ambiguities to the intent or scope of their usage in the specification and claims.

Promoter: Refers to sequences at the 5'-end of a structural gene involved in initiation of transcription. A plant-expressible promoter is any promoter capable of driving transcription in at least one type of plant cell in at least one developmental stage. Eukaryotic promoter sequences are commonly recognized by the presence of DNA sequences homologous to the canonical form 5'. . . TATAA . . . 3' about 10–30 base pairs (bp) 5'-to the location of DNA sequences encoding the 5'-end of a transcript (cap site). About 30 bp 5'-to the TATAA, another promoter sequence is often found which is recognized by the presence of DNA sequences homologous to the canonical form 5'. . . CCAAT . . . 3'.

Transcript Terminator

Refers herein to any nucleic acid sequence capable of determining the position of the 3'-end of a transcript. The transcript terminator DNA segment may itself be a composite of segments derived from a plurality of sources, naturally occurring or synthetic, prokaryotic, or eukaryotic, and may be from a genomic DNA or an mRNA-derived cDNA (mRNA: messenger RNA). Transcript termination sites include polyadenylation sites and sites determining the 3'-end of ribosomal RNAs (rRNAs), transfer RNAs (tRNAs), and nonpolyadenylated mRNAs (e.g. histone mRNA; Krieg, P. A. and Melton, D. A. (1984) Nature 308:203–206).

A polyadenylation site is a nucleic acid sequence correlated with polyadenylation of a transcript in eukaryotes, i.e. after transcriptional termination polyadenylic acid "tails" are added to the 3'-end of mRNA precursors. Polyadenylation sites are commonly recognized by the presence of homology to the canonical form 5'. . . AATAAA 3'. . . although variations of distance 5' to the 3'-end of the transcript, partial "read-through", and multiple tandem canonical sequences are not uncommon. DNA sequences between 20 and 35 bp downstream from the transcripts 3'-end seem to be necessary (McDevitt, M. A. et al. (1984) Cell 37:993–999). It should be recognized that a canonical "polyadenylation site" may actually determine the location of the 3'-end of the mRNA and not polyadenylation per se (Proudfoot, N. (1984) Nature 307:412–413; Birnstiel, M. L. et al. (1985) Cell 41:349–359).

Transcription Controlling Sequences

Refers to a promoter/transcript terminator site combination flanking a structural gene. The promoter and terminator DNA sequences flanking a particular foreign structural gene need not be derived from the same source genes (e.g. pairing two different T-DNA transcripts) or the same taxonomic source (e.g. pairing sequences from T-DNA with sequences from non-T-DNA sources such as plants, animals, fungi, yeasts, eukaryotic viruses, bacteria, and synthetic sequences).

Coat Protein Gene Transcript and Coat Protein mRNA

The former refers herein to the transcript of a plant-expressible coat protein gene while the latter refers herein to the coat protein-encoding mRNA present in nature during a viral infection. Although a "translatable transcript" will be recognized in the art to be a synonym for "messenger RNA", these two different terms are used herein to distinguish between the messenger synthesized during a viral infection and the product of the present invention's coat protein gene.

Coat Protein Gene

Refers herein to a promoter, a DNA sequence encoding a coat protein (i.e. coat protein structural gene), and a transcript terminator, the promoter, the structural gene, and the terminator having such position and orientation with respect to each other that, when in a plant cell, a coat protein-encoding transcript may be synthesized under control of the promoter and the terminator. A coat protein gene may be a composite of segments derived from a plurality of sources, naturally occurring or synthetic. A coat gene transcript may include sequences derived in whole or in part from prokaryotic DNA, eukaryotic DNA, episomal DNA, plasmid DNA, plastid DNA, genomic DNA, cDNA, viral DNA, viral cDNA, chemically synthesized DNA, or the like. It is further contemplated that a coat protein gene may contain one or more modifications in either the transcription control sequences, transcribed sequences, or viral cDNA, which could affect the biological activity or chemical structure of the coat protein, the rate of expression, or the manner of expression control. Such modifications include, but are not limited to mutations, insertions, deletions, and substitutions of one or more nucleotides, and modifications that do not alter function of the coat protein or coat protein transcript but which affect intercellular localization, transport, or stability of the coat protein or its transcript. DNA encoding a coat protein gene may be an uninterrupted structural gene or it may include one or more introns, bounded by the appropriate plant-functional splice junctions, which may be obtained from a synthetic or a naturally-occurring source.

cDNA (Complementary DNA)

Though this term is well-understood in the art, it has two meanings. (1) A cDNA can be a single-stranded DNA complementary to an RNA (e.g. a viral mRNA). (2) A cDNA can also be a double-stranded DNA segment, one strand of which is complementary to an RNA, the other strand having a sequence equivalent to that RNA (substituting T for U). Generally, a double-stranded cDNA is derived from a single-stranded cDNA. However, as defined herein, a double-stranded DNA encoding mRNA sequences, e.g. the DNA of a structural gene, is included within the term cDNA. In this Specification, the meaning of cDNA is defined by context and will be well-understood by those in the art.

Plus-Stranded

Refers to viruses having genomes having sequences equivalent to that of the virus' mRNA; i.e. RNA found in virus particles is not complementary to viral mRNA. Often the viral RNA of plus-stranded viruses can serve as an mRNA. AMV is an example of a plus-stranded virus; each of the four RNAs found in AMV virions is capable of serving as an mRNA. "Minus-strand," or antisense RNA, refers to the complement of the plus-strand.

Tripartite RNA Genome

Refers to organization of a virus' genetic material. "Genome" refers to the total genetic material of the virus. "RNA genome" states that as present in virions (virus particles), the genome is in RNA form. Tripartite indicates that the genome is divided among three separate RNA molecules. An example of a virus with a tripartite RNA genome is AMV. The genome of AMV is carried by AMV RNAs 1, 2, and 3. The sequence of RNA4 is totally contained by RNA3, and RNA4 is not replicated; therefore RNA4 is referred to as a subgenomic RNA and is not counted as one of the genomic RNAs.

Translational Initiation Site

Refers herein to the 5'AUG3' translational start codon at the 5'-end of a structural gene, the nucleotide following the AUG, and the 3 nucleotides preceding the AUG (see Kozak, M. (1983) Microbiol. Rev. 47:1–45, and Kozak, M. (1984) Nucl. Acids Res. 12:857–872).

5'-Untranslated Sequence

Refers herein to the part of an mRNA or transcript between its 5'-end, or "cap site", and the translational start codon.

Plant-Expressible Selectable or Screenable Marker

Refers herein to a genetic marker functional in a plant cell. A selectable marker (e.g. a kanamycin resistance gene) allows cells containing and expressing that marker to grow under conditions unfavorable to growth of cells not expressing that marker. A screenable marker (e.g. a beta-galactosidase gene) facilitates identification of cells which express that marker.

Essentially Full-Length cDNA

Refers herein to a cDNA that is complementary to an entire mRNA, possibly excepting a few (e.g. about five) nucleotides at either end of that mRNA sequence.

Transforming

Refers to the act of causing a cell to contain a nucleic molecule or sequence not originally part of that cell.

Plant Tissue

Includes differentiated and undifferentiated tissues of plants including, but not limited to roots, shoots, pollen, seeds, tumor tissue, such as crown galls, and various forms of aggregations of plant cells in culture, such as embryos and calluses. The plant tissue may be in planta or in organ, tissue, or cell culture.

Plant Cell

As used herein includes plant cells in planta and plant cells and protoplasts in culture.

The following terms are well-known in the art and are not specifically or specially defined herein: structural gene, single-stranded, genome, alfalfa mosaic virus group (see Matthews, R. E. F. 1982) Classification and Nomenclature of Viruses, p. 177), CaMV 19S promoter (see Hohn, T. et al. (1982) Curr. Top. Microbiol. Immunol. 96:193–236), octopine-type T-DNA (positions, orientations, and ORFs are defined as designated by Barker, R. F. et al. (1983) Plant Mol. Biol. 2:335–350), T-DNA border repeat, translatable, transcription under control of a promoter, ligating, descended, and structural gene.

Production of a genetically-modified cell expressing a coat protein gene combines the specific teachings of the present disclosure with a variety of techniques and expedients known in the art. In most instances, alternative expedients exist for each stage of the overall process. The choice of expedients depends on variables such as the choice of the particular virus to which resistance is desired, the basic vector system for the introduction and stable maintenance of the coat protein gene, the plant species to be modified, and the desired regeneration strategy, the particular transcriptional control sequences used, and the like, all of which present alternative process steps which those of ordinary skill are able to select and use to achieve a desired result. As novel means are developed for the stable insertion and transcription of foreign DNA in plant cells, those of ordinary skill in the art will be able to select among those alternate process steps to achieve a desired result. The fundamental aspects of the invention are the nature of the coat protein gene and its use to confer resistance to viral infections of plants transformed therewith. Other aspects include the nature and structure of the coat protein structural gene sequence and its means of insertion and expression in a plant genome. The remaining steps of the preferred embodiment for obtaining a genetically modified plant include inserting the coat protein gene into T-DNA, transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced coat protein gene, and other linked or co-transformed DNA sequences from the originally transformed strain into commercially-acceptable cultivars, and monitoring expression in transformed plants.

A starting point for construction of a coat protein gene is obtaining DNA clones of viral sequences. If the virus is a DNA virus, the DNA clones are obtainable using methods well-known in the art of recombinant DNA. If the virus is an RNA virus, a cDNA clone must be made from the viral sequence desired. A number of methods for making cDNA clones are known in the art of recombinant DNA; choice of methods will depend on variables such as polyadenylation, RNA length, prior knowledge of RNA sequence, prior preparations within the particular laboratory for other cDNA cloning experiments, and the like.

A principal feature of the present invention in its preferred embodiment is the construction of a T-DNA derivative having an inserted gene under control of a plant-expressible transcription controlling sequences, i.e., between a promoter and a transcript terminator, as these terms have been defined, supra. The coat protein-encoding structural gene must be inserted in correct position and orientation with respect to the promoter. Position relates to that side of the promoter on which the structural gene is inserted. It is known that the majority of promoters control initiation of transcription and translation in one direction only along the DNA. The region of DNA lying under promoter control is said to lie "downstream" or alternatively "behind" or "3' to" the promoter. Therefore, to be controlled by the promoter the correct position of a structural gene insertion must be "downstream" from the promoter. Orientation refers to the directionality of the structural gene. That portion of a coat protein-encoding DNA which encodes the amino terminus of a viral coat protein is termed the 5'-end of the structural gene, while that end which encodes amino acids near the carboxyl end of the protein is termed the 3'-end of the structural gene. Correct orientation of the coat protein-encoding DNA is with the 5'-end thereof proximal to the promoter. Similarly to the promoter region, the transcript terminator must be located in correct position and orientation relative to the coat protein structural gene, being proximal to the 3'-end of the structural gene. Differences in rates of coat protein gene expression or developmental control may be observed by varying coat protein structural gene-carrying components, promoters, transcript terminators, flanking DNA sequences, or site of insertion into the transformed plant's genome. Coat protein gene transcript accumulation may also be greatly influenced by the details of the coat protein gene transcript secondary structure, especially stem-loop structures. Different properties, including, but not limited to such properties as stability, intracellular localization, post-transcriptional processing, and other functional properties of the expressed coat protein gene itself may be observed when the gene's components are varied. All of these variations present numerous opportunities to manipulate and control the functional properties of the viral resistance phenotype, depending upon the desired physiological properties within the plant cell, plant tissue, and whole plant.

The fundamental principle of the present invention is that the presence of coat protein in a plant cell is capable of conferring at least some level of viral resistance to that cell. The present invention is not limited by the mode or mechanism of interference. The coat protein gene need not encode a full-length structural gene; any encoded coat protein structural gene derivative that interferes with viral infection is sufficient.

It is important to have enough coat protein present in a plant cell to be able to interfere with viral life cycle; if too little coat protein is present, infection will not be inhibited. Maximization of translation efficiency will help increase accumulation of coat protein. The art recognizes that several factors affect translational efficiency. These factors include codon usage, distance between the 5'-end of a translatable coat protein transcript ("cap-site") and the AUG translational start codon, transcript secondary structure, lack of AUG codons between the cap site and the translational initiation site, sequence of the translational initiation site, and the like. In general, evolution has already greatly optimized codon usage of coat protein structural genes. Excessively long 5'-untranslated sequences can lower translational efficiency; generally shorter "leader" sequences are desirable. Excessive double-stranded secondary structure, e.g. stem-loop structures, are thought to lower translational efficiency, though some secondary structure is thought to be needed for RNA function or stability. A consensus translational initiation site has been derived: 5'CCAGCCAUGG3' (see Kozak, M. (1986) Cell 44:283–292, and references cited therein, especially Kozak, M. (1983) Microbiol. Rev. 47:1–45, and Kozak, M. (1984) Nucl. Acids Res. 12:857–872) AUG being the translational start codon. Deviations from this consensus might lower translational efficiency. The presence of an AUG codon between the cap site and the translational start site is also known to lower translational efficiency (e.g. see Rogers, S. G. (1985) Plant Mol. Biol. Rep. 3:111–116).

As defined, the transcript of a coat protein gene may include nonviral sequences. Even in cases where a full-length viral sequence is included, a coat protein gene transcript may include nonviral sequences. Usually these nonviral sequences will be at the 5'- and 3'-ends of the coat protein transcript. Often these nonviral components will be derived from promoter or transcript terminator DNA segments. Inclusion of various nonviral sequences may affect RNA stability, cellular localization of the transcript, post-transcriptional processing, and the like. It is known to the art that RNA stability is affected by terminal structures such as 5'-capping and 3'-polyadenylation and by the extent of internal structure, i.e. intramolecular basepairing. A coat protein transcript may be localized within a cell, e.g. a transcript having a translatable sequence encoding a signal peptide-containing polypeptide will tend to be bound to rough endoplasmic reticulum. An intron may be included in a coat protein gene, provided that if the splice sites are derived from two different genes, the intron splice sites be compatible.

Combining of DNA segments including viral, nonviral, promoter, and transcript terminator sequences to form a coat protein gene, is accomplished by means known and understood by those of ordinary skill in the art of recombinant DNA technology. Choice of promoter depends on the developmental regulation desired. Use of developmentally-regulated promoters for gene expression in plants is described in the Background. T-DNA or CaMV promoters are advantageous as they are constitutive. The RuBP-Case small subunit promoter may be useful for expression in the green tissues of coat protein gene-transformed plant. In the preferred embodiments, the transcript terminator is a polyadenylation site. The plant gene source of the polyadenylation site is not crucial provided that the polyadenylation site, the promoter and the coat protein structural gene are compatible for transcription and post-transcriptional processing.

As will be apparent to those of ordinary skill in the art, the coat protein gene combination may be placed between any restriction sites convenient for removing the combination from the plasmid it is carried on and convenient for insertion into the plant transformation vector of choice. For example, location of the coat protein gene insertion site within T-DNA is not critical as long as the transfer function of sequences immediately surrounding the T-DNA borders are not disrupted, since in prior art studies these regions appear to be essential for insertion of the modified T-DNA into the plant genome. The combination is inserted into the plant transformation vector by standard techniques well-known to those skilled in the art. The orientation of the assembled coat protein gene, with respect to the direction of transcription and translation of endogenous vector genes is not usually critical; generally, either of the two possible orientations is functional.

As reviewed in the Background (Ti Plasmid DNA), T-DNA of micro-Ti plasmids can be transferred from an Agrobacterium strain to a plant cell provided the Agrobacterium strain contains certain trans-acting genes whose function is to promote the transfer of T-DNA to a plant cell. Micro-Ti plasmids are advantageous in that they are small and relatively easy to manipulate directly, eliminating the need to transfer the gene to T-DNA from a shuttle vector by homologous recombination. After the desired coat protein gene has been inserted, they can easily be introduced directly into an Agrobacterium cell containing trans-acting vir genes, the vir genes usually being on a "helper plasmid", that promotes T-DNA transfer. Introduction into an Agrobacterium strain is conveniently accomplished either by transformation of the Agrobacterium strain or by conjugal transfer from a donor bacterial cell, the techniques for which are well-known to those of ordinary skill. For purposes of introduction of novel DNA sequences into a plant genome, Ti plasmids, Ri plasmids, micro-Ti plasmids, and T-DNA integrated into chromosomes should be considered functionally equivalent.

T-DNA having a coat protein gene can be transferred to plant cells by any technique known in the art. For example, this transfer is most conveniently accomplished by co-cultivation of the Agrobacterium strain with plant cells or with plant tissues. Using these methods, a certain proportion of the plant cells are transformed, that is to say have T-DNA transferred therein and inserted in the plant cell genome. In either case, the transformed cells must be selected or screened to distinguish them from untransformed cells. Selection is most readily accomplished by providing a selectable marker incorporated into the T-DNA in addition to the coat protein gene. Examples of artificial markers include those reviewed in the Background (see the sections on Chimeric Genes). In addition, the T-DNA provides endogenous markers such as gene(s) controlling abnormal morphology of Ri-induced tumor roots and gene(s) that control resistance to toxic compounds such as amino acid analogs, such resistance being provided by an opine synthesizing enzyme (e.g. ocs). Screening methods well-known to those skilled in the art include, but are not limited to assays for opine production, specific hybridization to characteristic nucleic acid sequences (e.g. coat protein transcripts or T-DNA) or immunological assays for specific proteins (e.g. coat protein). Additionally, a phenotype of an expressed coat protein gene (e.g. resistance to a target virus) can be used to identify transformed tissue. Assay of viral resistance may be done by one of a number of methods well-known in the art of plant virology, including detection of decreased production of a virus component (e.g. a viral RNA or a viral protein), decreased infectivity as assayed by protoplast infection or local lesion assays, decreased production of progeny virus, and the like.

Although the preferred embodiments involve use of micro-Ti plasmids, other T-DNA-based vector systems known to the art may readily be substituted. Furthermore, though the preferred embodiment of this invention incorporates a T-DNA-based Agrobacterium-mediated system for incorporation of the coat protein gene into the genome of the plant which is to be transformed, other means for transferring and incorporating the coat protein gene are also included within the scope of this invention. Other means for the stable incorporation of the coat protein gene into a plant genome additionally include, but are not limited to use of vectors based upon viral genomes, minichromosomes, transposons, and homologous or nonhomologous recombination into plant chromosomes. Alternate forms of delivery of these vectors into a plant cell additionally include, but are not limited to fusion with vector-containing liposomes or bacterial spheroplasts, microinjection, encapsidation in viral coat protein followed by an infection-like process, and direct uptake of DNA, possibly after induction of plasmalemma permeability by an electric pulse, a laser, or a chemical agent. Means for transient incorporation and/or expression are also included within the scope of this invention. Systems based on Agrobacterium cells and T-DNAs can be used to transform angiosperms, including dicots and monocots, by transfer of DNA from a bacterium to a plant cell; systems based on alternate vectors or means for vector delivery may be used to transform gymnosperms and angiosperms.

Regeneration of transformed cells and tissues is accomplished by resort to known techniques. An object of the regeneration step is to obtain a whole plant that grows and reproduces normally but which retains integrated T-DNA. The techniques of regeneration vary somewhat according to principles known in the art, and may depend upon the plant transformation vector and the species of the transformed plant. Regeneration of transformed tobacco plants, petunia plants, and plants of related species is well-known to the art. As means for regeneration of other plant species are developed, the art will understand, without undue experimentation, how to adapt these newly-discovered means for regeneration of plants from transformed plant cells and transformed plant tissues.

The genotype of the plant tissue transformed is often chosen for the ease with which its cells can be grown and regenerated in in vitro culture and for susceptibility to the selective agent to be used. Should a cultivar of agronomic interest be unsuitable for these manipulations, a more amenable variety is first transformed. After regeneration, the newly introduced coat protein gene may be readily transferred to the desired agronomic cultivar by techniques well-known to those skilled in the arts of plant breeding and plant genetics. Sexual crosses of transformed plants with the agronomic cultivars yield initial hybrids. These hybrids can then be back-crossed with plants of the desired genetic background. Progeny are continuously screened and/or selected for the continued presence of integrated coat protein gene DNA, T-DNA, or for a new phenotype resulting from expression of the coat protein gene or other genes carried by the inserted DNA. In this manner, after a number of rounds of back-crossing and selection, plants can be produced having a genotype essentially identical to the agronomically-desired parents with the addition of inserted DNA sequences.

An alternative to incorporation of a coat protein gene into a plant genome for making a coat protein-containing plant cell is to infect a plant with a vector viral RNA capable of being maintained in that plant, the viral RNA having coat protein-encoding sequences of a target virus (i.e. a virus from which one wants protection that is distinct from the vector virus). Typically, double-stranded cDNA sequences of the vector virus and the target virus are manipulated using recombinant DNA technology. After assembly of a DNA sequence corresponding to that of the desired vector RNA/target coat protein cDNA combination, the plant viral vector cDNA/coat protein cDNA combination may be placed behind a promoter that can drive in vitro transcription. Descriptions of such vectors and conditions for their use include Melton, D. A. et al. (1984) Nucl. Acids Res. 12:7035–7056; Krieg, P. A. and Melton, D. A. (1984) Nucl. Acids Res. 12:7057–7070; Ahlquist, P. and Janda, M. (1984) Mol. Cell. Biol. 4:2876–2882; and French, R. et al. (1986) Science 231:1294–1297. After such a viral vector/target coat protein/in vitro transcription vector combination is assembled, a viral vector RNA/target coat protein sequence combination may be produced by in vitro transcription and mixed with any other viral RNA components necessary for maintenance of the viral vector in a plant cell. Infection by a vector/coat protein sequence combination of a plant cell may then be effected by known methods and, after inoculation with the target virus or target virus RNA, inhibition of infection or production of a viral component may be assayed by methods well-known in the art. Using such methods, high levels of coat protein transcript and coat protein may be accumulated.

Similarly, plant viral DNA vectors may be used to introduce a coat protein gene into a plant cell. The utility of such vectors has been demonstrated by Brisson, N. et al. (1984) Nature 310:511–514. The means for creating functional coat protein genes as taught by the present invention can be combined with use of plant DNA virus-based vectors by those of ordinary skill in the art. After infection of an appropriate plant host cell, inhibition of target virus infection may be assayed as described above.

EXAMPLES

The following Examples are presented for the purpose of illustrating specific embodiments within the scope of the present invention without limiting the scope, the scope being defined by the claims. Numerous variations will be readily apparent to those of ordinary skill in the art.

The Examples utilize many techniques well-known and accessible to those skilled in the arts of molecular biology and manipulation of T-DNA and Agrobacterium; such methods are fully described in one or more of the cited references if not described in detail herein. All references cited in this Specification are hereby incorporated by reference.

Enzymes are obtained from commercial sources and are used according to the vendors' recommendations and other variations known to the art. Reagents, buffers, and culture conditions are also known to those in the art. Reference works containing such standard techniques include the following: Wu, R. (ed.) (1979) Methods Enzymol. 68; Wu, R. et al. (eds.) (1983) Methods Enzymol. 100 and 101; Grossman, L. and Moldave, K. (eds.) (1980) Methods Enzymol. 65; Weissbach, A. and Weissbach, H. (eds.) (1986) Methods Enzymol. 118 (see especially Rogers, S. G. et al. pp. 627–640); Miller, J. H. (1972) Experiments in Molecular Genetics; Davis, R. et al. (1980) Advanced Bacterial Genetics; Schleif, R. F. and Wensink, P. C. (1982) Practical Methods in Molecular Biology; Walker, J. M. and Gaastra, W. (eds.) (1983) Techniques in Molecular Biology; and Maniatis, T. et al. (1982) Molecular Cloning. Additionally, Lathe, R. F. et al. (1983) Genet. Eng. 4:1–56, make useful comments on DNA manipulations.

Textual use of the name of a restriction endonuclease in isolation, e.g. "BclI", refers to use of that enzyme in an enzymatic digestion, except in a diagram where it can refer to the site of a sequence susceptible to action of that enzyme, e.g. a restriction site. In the text, restriction sites are indicated by the additional use of the word "site", e.g. "BclI site". The additional use of the word "fragment", e.g. "BclI fragment", indicates a linear double-stranded DNA molecule having ends generated by action of the named enzyme (e.g. a restriction fragment). A phrase such as "BclI/SmaI fragment" indicates that the restriction fragment was generated by the action of two different enzymes, here BclI and SmaI, the two ends resulting from the action of different enzymes.

Plasmids, and only plasmids, are prefaced with a "p", e.g., pti15955 or pH400, and strain designations parenthetically indicate a plasmid harbored within, e.g., A. tumefaciens (pTi15955) or E. coli K802 (pH400). The following strains are on deposit and will be made available to the art upon grant of letters patent:

| E. coli MC1061 (pH400A4) | NRRL B-18061 |
| E. coli K802 (pH4-1) | NRRL B-18009 |
| A. tumefaciens (pTi15955) | ATCC 15955 |
| E. coli CSH52 (pSUP106) | NRRL B-15486 |
| E. coli SM10 | NRRL B-15481 |
| E. coli S17-1 | NRRL B-15483 |

(ATCC: American Type Culture Collection, 12301 Parklawn Dr., Rockville, Md. 20852 USA; NRRL: ARS Patent Collection, Northern Regional Research Center, 1815 N. University St., Peoria, Ill. 61604 USA.) Other plasmids and strains are widely available and accessible to those in the art.

Example 1

Preparation of AMV RNA4 cDNA pSP65A4 (Loesch-Fries, L. S. et al. (1985) Virol. 146.:177–187) carries a full-length cDNA copy of AMV RNA4 in pSP65. pSP65 is designed for in vitro transcription under control of a bacteriophage SP6 promoter (Melton, D. A. et al. (1984) Nucl. Acids Res. 12:7035–7056; Krieg, P. A. and Melton, D. A. (1984) Nucl. Acids Res. 12:7057–7070). pSP65A4 directs synthesis of AMV coat protein-encoding sequences. When it is cut by SmaI and EcoRI in vitro run-off transcripts are essentially full-length coat protein mRNA sequence.

Example 2 preparation of CaMV transcription controlling sequences pDOB512, carrying cauliflower mosaic virus (CaMV) transcription controlling sequences (obtained from Dr. Ken Richards, Centre National de la Recherche Scientifique, Institute de Biologie Moleculaire et Cellulaire, 15, rue Descartes, F-67084 Strasbourg, France) was constructed as follows: (For a review of CaMV, see Hohn, T. et al. (1982) Curr. Top. Microbiol. Immunol. 96:193–236.) A HindIII fragment carrying the CaMV 19S RNA promoter region (CaMV nucleotides 5376–5851) was inserted into pBR322 and was trimmed back to within one base pair of the 19S transcript cap site. A HincII fragment carrying the CaMV 19S transcript terminator (CaMV nucleotides 7018–7794) to which BamHI linkers had been added was then inserted behind the 19S promoter; the resulting plasmid is designated pDOB412. pDOB412 DNA was digested with BglII and SalI, filled in by the Klenow fragment of *E. coli* DNA polymerase I, and religated, thereby deleting DNA, which includes BamHI and HindIII sites, between the CaMV position 7644 BglII site and the pBR322 position 650 SalI site and regenerating a BglII site. The resultant plasmid was designated pDOB512.

The sticky-ends of HindIII linearized pDOB512 DNA were filled in by Klenow fragment (or alternatively by T4 DNA polymerase). The blunt-ended pDOB512 DNA was mixed with and ligated to commercially-available BglII linkers. The ligation mix was then transformed into *E. coli* K802 and an ampicillin-resistant transformant was isolated which harbored a plasmid designated pDOB513. pDOB513 has CaMV 19S transcription controlling sequences on a BglII fragment. SmaI and BamHI sites are found between the DNA segments having the promoter and the polyadenylation site in both pDOB412, pDOB512, and pDOB513, thereby providing a convenient location for insertion of foreign DNA that is to be a template for a transcript.

Example 3

Placement of AMV cDNA behind the CaMV promoter pSP65A4 DNA was digested with EcoRI and SmaI and the 0.89 kbp AMV cDNA was purified by elution from an agarose gel after electrophoretic separation. The EcoRI sticky-end was converted to a blunt-end by incubation with the Klenow fragment of *E. coli* DNA polymerase I. After SmaI-linearized pDOB513 DNA was mixed with and ligated to the blunt-ended cDNA, the ligation products were transformed into MC1061. Ampicillin-resistant transformants were screened by colony hybridization to an AMV RNA4 probe. A colony was identified harboring a plasmid, designated pDOBA4, having AMV cDNA inserted between CaMV 19S transcription controlling sequences oriented so that when transcribed, a coat protein-encoding transcript would be synthesized; i.e. so that the EcoRI end and an internal BamHI site are proximal to the promoter and distal to the transcript terminator. A CaMV transcription controlling sequences/AMV coat protein structural gene combination may be removed from pDOBA4 on a 1.92 kbp BglII fragment.

Example 4

Construction of pH400, a micro-Ti plasmid pH4-1 is a micro-Ti plasmid harbored by *E. coli* K802 (pH4-1), which is on deposit as NRRL B-18009. pH4-1 is disclosed by Dahl, et al. U.S. patent application Ser. No. 144,016, filed Jan. 13, 1988, now U.S. Pat. No. 4,921,802, issued May 1, 1990, and its parent application, Sutton et al., U.S. patent application Ser. No. 788,984, filed Oct. 21, 1985 which is hereby incorporated by reference, and by Merlo, D. et al. (1985) Abstracts, 1st Int. Cong. Plant Mol. Biol., Galau, G. A. (ed.). pH4-1 contains two T-DNA fragments, a HindIII fragment spanning positions 602 and 2,290 (as defined by Barker, R. F. et al. (1983) Plant Mol. Biol. 2:335–350) carrying the left border of TL and promoter sequences associated with ORF1, and a SmaI/BclI fragment spanning positions 11,207 and 14,711, having, a 3'-deleted tml, an intact ocs, and the right border of TL. Between the position 3,390 HindIII site and the position 11,207 SmaI site (this SmaI site having been converted to a BglII by site insertion of BglII linkers) of these two fragments is a plant-expressible selectable marker. This marker has a CaMV 19S promoter, a Tn5 kanamycin resistance structural gene encoding neomycin phosphotransferase II, and two polyadenylation sites, one from CaMV and another from T-DNA ORF26, donated by a T-DNA fragment spanning HincII sites at positions 21,727 and 22,440. The kanamycin resistance gene is oriented parallel to ocs and tml and antiparallel to the ORF1 promoter. The T-DNA/selectable marker combination is inserted into the HindIII site of pSUP106, an 11 kbp wide host-range plasmid capable of maintenance in both *E. coli* and Agrobacterium (Priefer, U. B. et al. (1985) J. Bacteriol. 163:324–330; *E. coli* CSH52 (pSUP106) is on deposit as NRRL B-15486). The T-DNA is oriented within pSUP106 so that the TL right border is proximal to the pSUP106 EcoRI site, which is present within pSUP106 chloramphenicol resistance gene.

pH4-1 has two BglII sites, both of which flank the kan selectable marker. One of the BglII sites was removed, thereby leaving a unique BglII site useful for insertion of extraneous coding DNA, as follows: pH4-1 DNA was linearized by being partially digested with BglII and full-length, linear DNA was electrophoretically isolated. The BglII sticky-ends were then removed by incubation with the Klenow fragment of *E. coli* DNA polymerase I. The resulting blunt-ended DNA was ligated to itself and transformed into *E. coli*. Plasmid DNAs isolated transformants resistant to chloramphenicol were screened by restriction analysis and a colony was identified which harbored a plasmid designated pH400. pH400 was identical to pH4-1 except for the absence of the BglII site between the kan gene and the ORF1 promoter, the unique pH400 BglII site being located between the kan gene and the ocs gene.

Example 5

Insertion of an AMV4 coat protein gene into pH400 pDOBA4 DNA was digested with BglII and then mixed with and ligated to BglII-linearized, dephosphorylated pH400 DNA. After transformation into MC1061 and selection for chloramphenicol resistance, plasmid DNAs were characterized by restriction analysis. A colony was identified which harbored a plasmid, designated pH400A4, having a coat protein gene inserted into the pH400 BglII site. pH400A4 has a coat protein gene having full-length AMV RNA4 sequences, the gene being oriented parallel to the 3'-deleted tml gene, ocs, and the kanamycin selectable marker.

Example 6

Plant transformation pH400A4 was transferred into *A. tumefaciens* LBA4404 (Ooms, G. et al. (1981) Gene 14:33–50), a vir gene-harboring, micro-Ti-mobilizing strain, by the triparental mating technique. (Ruvkun, G. B. and Ausubel, F. M. (1981) Nature 289:85–88), which is well-known in the art, or by mating from a mobilizing strain of *E. coli*, e.g. SM10 (NRRL B-15481) or S17-1 (NRRL B-15483) (Simon, R. et al. (1983) Biotechnol. 1:784–791). Tobacco leaf tissue was obtained from 4- or 5-week old XanthiNC plants grown axenically in Magenta boxes. Inoculation was by a modification of the method of Horsch, R. B. et al. (1985) Science 227:1229–1231. Inocula were prepared by placing two loopfuls of Agrobacteria in 10 ml of L-broth. After suspension by forceful pipetting with a Pasteur pipette, inocula could be used immediately. Leaves were excised and midribs were removed; cutting surfaces were wetted with L-broth to help keep the leaves wet. Leaf pieces were about 2–4 mm wide and about 7–10 mm long. Leaf segments were dipped in the inoculum for 5–10 minutes, though in some experiments leaf pieces were just briefly dipped into the inoculum or were infiltrated with the inoculum in a vacuum flask. Pieces were then blotted dry on sterile filter paper and placed upside down on feeder plates prepared from a Xanthi suspension culture. The feeder plates had a SMPi medium (SMpi: MX- supplemented with 0.1 mg/l p-chlorophenoxyacetic acid (pCPA) and 7.5 mg/l 6-(8,8-dimethylallylamino)purine (2iP); MX-: 1.65 g/l $NH_4NO_3$, 1.9 g/l $KNO_3$, 440 mg/l $CaCl_2.2H_2O$, 370 mg/l $MgSO_4.7H_2O$, 170 mg/l $KH_2PO_4$, 0.83 mg/l KI, 6.2 mg/l $H_3BO_3$, 22.3 mg/l $MnSO_4.4H_2O$, 8.6 mg/l $ZnSO_4.7H_2O$, 0.25 mg/l $Na_2MoO_4.2H_2O$, 0.025 mg/l $CoCl_4.5H_2O$, 37.23 mg/l $Na_2EDTA$, 27.85 mg/l $FeSO_4 2.7H_2O$, 1 g/l inositol, 50 mg/l nicotinic acid, 50 mg/l pyroxidineHCl, 50 mg/l thiamineHCl, 30 g/l sucrose, pH 5.8, solidified with 8 g/l agar). Leaf pieces were removed from feeder plates after 4–6 days and placed on SMPi medium supplemented with 500 mg/l carbenicillin, 50 mg/l cloxacillin, and 100–300 mg/l kanamycin (200 mg/l optimum). The resulting shoots were excised and placed on MX- medium supplemented with 100–300 mg/l kanamycin (200 mg/l optimum).

Example 7

Expression in tobacco

Regenerated tobacco plants descended from cells transformed by *A. tumefaciens* LBA4404 (pH400A4) were self-fertilized. Presence of coat protein in transformants was confirmed by an enzyme-linked immunosorbant assay (ELISA) (Table 1) and presence of a coat protein gene transcript was confirmed by Northern blot analysis. Coat protein-containing tobacco plants were challenged by inoculating carborundum-abraded leaves with AMV virions.

TABLE 1

EXPRESSION OF COAT PROTEIN IN TRANSFORMED TOBACCO

| Expression | | Coat Protein Level of | |
|---|---|---|---|
| Transformant | Octopine | (ng/ml sap) | ng/mg protein |
| 14-1 | − | 2970 | 100 |
| 14-5 | + | 2318 | 210 |
| 27-4 | + | 131 | 21 |
| 27-35 | + | 591 | 48 |
| 37-2 | + | 1327 | 101 |
| 37-4 | + | 1410 | 176 |
| 37-5 | + | 502 | 51 |
| 37-6 | − | 2263 | 342 |

When compared to control plants, plants having coat protein were observed to be resistant to AMV infection or to have reduced or delayed symptoms, depending on the level of coat protein in tissues of a particular plant. Results were disclosed by Loesch-Fries, L. S. et al. (1987) EMBO J. 6:1845–1851, which is hereby incorporated by reference.

Example 8

In vitro tests of coat protein functions in tobacco

The establishment of an AMV infection is known to be coat protein dependent. This coat protein may be supplied as part of an inoculum (either as free coat protein or in the form of virions) or may be synthesized early in the infection process if RNA4 is present in the inoculum. If the transformed protoplasts contain coat protein, establishment of infection should no longer be dependent on the presence in the inoculum of coat protein or its messenger RNA. Tobacco protoplasts were prepared and inoculated essentially as described by Samac, D. A. et al. (1983) Virol. 131:455–462. A major modification was that RNA was added in a small volume (e.g. 10 l) to the protoplast pellet, which was then resuspended in residual supernatant before addition of polyethylene glycol (PEG). Inoculations of coat protein-containing protoplasts with an RNA preparation lacking AMV RNA4 gave very high levels of infection; similar inoculations of untransformed protoplasts gave essentially no infection (Table 2). Indeed, levels of infection of transformed protoplasts with

TABLE 2

BIOLOGICAL ACTIVITY OF EXPRESSED COAT PROTEIN

| | Infected Protoplasts (%) | | |
|---|---|---|---|
| Inoculum* | Nontransformed protoplasts | Transformant 14-1 protoplasts | Transformant 14-5 protoplasts |
| AMV RNA 1 + 2 + 3 | 0 | 63 | 30 |
| AMV RNA 1 + 2 + 3 + 4 | 33 | 61 | 66 |
| unfractionated AMV RNA | 69 | 85 | 77 |

*Inoculum for 105 protoplasts consisted of 0.6 g of AMV RNA 1 + 2 + 3 alone or in combination with 1 g AMV RNA 4 or 6 g of unfractionated AMV RNA. RNA uptake occurred in the presence of PEG—$CaCl_2$. Infection was assayed by immunofluorescence using antibodies to coat protein.

preparations lacking coat protein mRNA were even higher than observed for inoculation of untransformed protoplasts with RNA preparations having all four components. This demonstrated that the coat protein contained by transformed protoplasts was biologically active.

Tobacco protoplasts were infected in vitro with AMV virions essentially as described above for RNA. In a typical experiment using tobacco protoplasts derived from transformed or control tobacco plants, protoplasts which contained coat protein as assayed by ELISA had significantly lower levels of infection than control protoplasts (Table 3). Although levels of protection varied, infection levels for protoplasts containing AMV coat protein were always less than observed for untransformed controls. This demonstrated that the presence of AMV coat protein in a plant cell can protect that cell from infection by alfalfa mosaic virus. Results are disclosed in detail by Loesch-Fries, L. S. et al. (1987) in *Molecular Strategies for Crop Protection*, Arntzen, C. J. and Ryan, C. f (eds.), Alan R. Liss, Inc., pp. 221–234, which is hereby incorporated by reference.

Example 9

Transformation of alfalfa

Odell, J. T. et al. (1985) Nature 313:810–812, disclose a deletion series of DNA fragments spanning the region carrying the cauliflower mosaic virus (CaMV) 35S promoter.

TABLE 3

PROTECTIVE EFFECTS OF COAT PROTEIN IN TRANSFORMED TOBACCO

| Protoplast Source | Coat Protein (ng/107 protoplasts) | Infected protoplasts (%)* |
|---|---|---|
| Experiment 1 | | |
| Untransformed tobacco Transformant | 0 | 62 |
| 14-1 | 38 | 32 |
| 101 | 131 | 5 |
| 102 | 56 | 9 |
| 107 | 45 | 17 |
| 108 | 10 | 26 |
| Experiment 2 | | |
| Untransformed tobacco Transformant | ND | 98 |
| 14-1 | ND | 21 |
| 14-5 | ND | 44 |
| Experiment 3 | | |
| Untransformed tobacco Transformant | 0 | 50 |
| 14-1 | 3.9 | 9 |
| 101 | 132 | 11 |
| 305 | 1.2 | 56 |
| 306 | 0.4 | 36 |

*Inoculum for 105 protoplasts consisted of 1–3 g alfalfa mosaic virus. Virus uptake occurred in the presence of PEG—$CaCl_2$. Infection was assayed by immunofluorescence using antibodies to coat protein.
ND = Not Determined.

An 833 base pair (bp) fragment was cut out of the pUC13 clone carrying the "–343" deletion by digestion with SmaI and HindIII. This fragment carries a functional 35S promoter and the 5'-end of the CaMV 35S transcript, spanning from position –343 to position +9 relative to the transcriptional start site. This fragment was ligated into pIC-19R (Marsh, J. L. et al. (1984) Gene 32:481–485) which had been digested with NruI and HindIII. The resulting plasmid was named pIC19R-35S.

A polyadenylation site from the T-DNA ORF25 gene spanning HincII sites at coordinates 21,727 and 22,440 (ORFs and coordinates as designated by Barker, R. F. et al. (1983) Plant Mol. Biol. 2:335–350) was obtained as a HincII fragment and ligated to SmaI-linearized pIC-19H DNA (Marsh, et al. supra), position 21,727 being proximal to the pIC-19H BamHI site. The resulting plasmid was cut with BamHI and BglII, and the T-DNA-containing fragment was ligated to BamHI-linearized pIC19R-35S DNA, position 21,727 being proximal to the CaMV 35S promoter. The polylinker SmaI site of the resulting plasmid was opened and a linker having sequence 5'CAGATCTGCA-GATCTGC3' and encoding a PstI site flanked by two BglII sites was inserted. The resulting plasmid was designated pIC35/A.

pIC35/A DNA was opened at the HincII (SalI) site in the polylinker between the promoter and polyadenylation site segments and ligated to a 0.89 kbp cDNA fragment prepared as described in Example 3. A plasmid having the AMV cDNA oriented so that a coat-protein encoding transcript could be transcribed by the 35S promoter was designated pIC35/A-A4.

The plant transformation vector pH575 was disclosed by Sutton, D. W. et al., European patent publication 0,223,417 (priority document being U.S. patent application Ser. No. 788,984, continued-in-part by U.S. patent application Ser. No. 144,016, which are hereby incorporated by reference). The 35S promoter/RNA4 cDNA/ORF25 polyadenylation site was removed from pIC35/A-A4 on a BglII fragment and inserted into BglII-linearized pH575 DNA. The resulting plasmid was designated pH57535SA4. This plasmid was introduced into A. tumefaciens LBA4404 prior to transformation.

Alfalfa (Medicago sativa L.) plants previously tested for regeneration potential were grown under sterile conditions on MX- in Magenta boxes. Trifoliate leaves were removed from plants. Then each leaflet was sliced into about 3–4 mm squares and placed for 10 to 90 min. in an Agrobacterium culture (OD=0.5–0.8 at 660 nm) in L-broth. Tissue pieces were then incubated about 2 days at 25° C. to 27° C. on modified B5H medium (modified B5H=1.18 g/l $CaCl_2.2H_2O$, 0.75 mg/l KI, 0.025 mg/l $CoCl_2.6H_2O$, 134 mg/l $(NH_4)_2SO_4$, 3 g/l $KNO_3$, 0.5 g/l $MgSO_4.7H_2O$, 10 mg/l $MnSO_4.H_2O$, 2 mg/l $ZnSO_4.7H_2O$, 0.0246 mg/l $CuSO_4.5H_2O$, 169 mg/l $NaH_2PO_4.2H_2O$, 3 mg/l $H_3BO_3$, 0.25 mg/l $Na_2MoO_4.2H_2O$, 0.3 g/l L-glutamine, 0.1 g/l serine, 1 mg/l adenine sulfate$2H_2O$, 10 mg/l L-glutathione, 27.84 mg/l $FeSO_4.2H_2O$, 37.24 mg/l Na2EDTA, 1 mg/l nicotinic acid, 1 mg/l pyridoxineHCl, 10 mg/l thiamineHCl, 0.5 g/l proline, 30 g/l sucrose, and 8 g/l agar (Taiyo) (B5h: Atanassov, A. and Brown, D. C. W. (1984) Plant Cell Tis. Org. Cult. 149–162). It was discovered that the use of high concentrations of kanamycin as disclosed in the prior art were toxic to transformed tissues. Accordingly, after rinsing 3 times in water, the pieces were cultured on modified B5H medium supplemented with reduced (20 mg/l) kanamycin and 100 mg/l cefoxitin, the pieces being transferred to fresh medium every 2 weeks. Calli formed on the edge of the leaf pieces in about 6 or 8 weeks. After a callus grew to be about 3 to 4 mm, it was separated from the leaf piece. Calli of genotypes which spontaneously formed embryos were plated directly on SH- medium (SH-=0.2 g/l $CaCl_2.2H_2O$, 2.5 g/l $KNO_3$, 0.4 g/l $MgSO_4.7H_2O$, 0.3 g/l $NH_4H_2PO4$, 5 mg/l $H_3BO_3$, 0.1 mg/l $CoCl_2.6H_2O$, 0.2 mg/l $CuSO_4.5H_2O$, 10 mg/l $MnSO_4.H_2O$, 1 mg/l $ZnSO_4.7H_2O$, 1 mg/l KI, 0.1 mg/l $Na_2MoO_4.2H_2O$, 15 mg/l $FeSO_4.7H_2O$, 20 mg/l $Na_2$ EDTA, 5 mg/l nicotinic acid, 5 mg/l thiamineHCl, 0.5 mg/l pyridoxineHCl, 1 g/l myo-inositol, 30 g/l sucrose, and 8% agar (Taiyo), pH5.8 (Schenk, R. U. and Hildebrandt, A. C. (1972) Can. J. Bot. 50:199–204)). Calli which did not spontaneously form embryos were induced for 7 days on modified B5H medium, supplemented with 11 mg/l 2,4-D and 1.0 mg/l kinetin, before transfer to SH-. Embryos were separated from the callus as they appeared and were allowed to germinate on SH- medium. When well rooted, plants were transplanted into a 50:50 peat:pearlite mix and hardened-off for a week under low light, high humidity conditions in a growth chamber.

Example 10

In vitro test of coat protein functions in alfalfa

Protoplasts were prepared from transformed alfalfa plants, infected with AMV, and assayed by ELISA for coat protein (CP), essentially as described by Loesch-Fries, et al. (1985) Virology 146:177–187. ELISA values are nonabsolute but do indicate relative levels. Results derived from two genotypes, designated herein as A and B, are presented in Table 4. For each genotype, several plants, all derived from the same callus, were tested. An untransformed, regenerated plant of either genotype A or B served as a control. Alfalfa protoplasts from plants having high AMV coat protein expression were significantly protected from infection by AMV virions; protoplasts from plants with low coat protein levels were marginally protected. As expected, the presence of coat protein did not protect protoplasts from infection by a mixture of AMV RNAs 1, 2, and 3; indeed the presence of coat protein in

TABLE 4

PROTECTIVE EFFECTS OF COAT PROTEIN
IN TRANSFORMED ALFALFA

| Genotype | Plant | ng CP per mg protein | % protoplasts infected: transformants (controls) | |
|---|---|---|---|---|
| | | | virus | RNAs 1, 2, 3 |
| A | 1 | 7 | | |
| | 3 | 7 | 27 (48) | 25 (5) |
| | 4 | 5 | 27 (22) | |
| | 6 | 10 | | |
| | 7 | 6 | | |
| | 8 | 6 | | |
| B | 1 | 160 | | |
| | 2 | 210 | <2 (72) | |
| | 3 | 150 | <1 (37) | |
| | 4 | 330 | 4 (37) | |
| | 5 | 440 | 1 (72) | |
| | 6 | 250 | 2 (47) | |
| | 7 | 160 | <2 (47) | | protoplasts improved infection over that of the controls. (In the controls, the coat protein required for establishment of infection came from contaminating RNA4).

We claim:

1. A DNA molecule comprising a plant-expressible promoter region upstream from a coat protein structural gene of a plant virus having a single-stranded, plus-stranded, tripartite RNA genome, wherein the promoter region causes transcription of a coat protein-encoding RNA, and wherein said DNA molecule does not encode additional genes of said plant virus.

2. A DNA according to claim 1, wherein the virus is of the alfalfa mosaic virus group.

3. A DNA according to claim 2, wherein the virus is AMV.

4. A DNA according to claim 3, wherein the virus is AMV strain 425.

5. A plant, that is uninfected by a virus and that comprises plant cells comprising the DNA of claim 1, whereby said plant is resistant to infection by said virus.

6. A plant that is uninfected by a virus and that comprises plant cells comprising the DNA of claim 2, whereby said plant is resistant to infection by said virus.

7. A plant that is uninfected by a virus and that comprises plant cells comprising the DNA of claim 3, whereby said plant is resistant to infection by said virus.

8. A plant that is uninfected by a virus and that comprises plant cells comprising the DNA of claim 4, whereby said plant is resistant to infection by said virus.

9. A plant according to claim 7, wherein said plant is an alfalfa plant.

10. A method for producing a virus-resistant plant comprising the steps of:

(a) making a DNA segment encoding a viral coat protein structural gene, wherein the coat protein encoded is that of a plant virus having a single-stranded, plus-stranded tripartite RNA genome, and ligating the structural gene segment to a plant-expressible promoter, the promoter being upstream from the structural gene such that a coat protein-encoding RNA may be transcribed under control of the promoter;

(b) transforming a transformable, regenerable plant cell to contain said DNA segment comprising said coat protein gene; and (c) regenerating said plant cell to produce a virus-resistant plant.

11. A method according to claim 10, wherein the coat protein is of a virus of the alfalfa mosaic virus group.

12. A method according to claim 11, wherein the virus is AMV.

13. The method of claim 12 wherein said plant is an alfalfa plant.

14. A plant cell comprising the DNA molecule of claim 1, 2, 3, or 4.

15. A bacterial cell comprising the DNA molecule of claim 1, 2, 3, or 4.

16. The bacterial cell according to claim 15, wherein said bacterial cell is an *E. coli* cell.

17. The bacterial cell according to claim 15, wherein said bacterial cell is an *Agrobacterium tumefaciens* cell.

18. A seed of the plant as claimed in claim 5, 6, 7, or 8.

19. A plant transformation vector comprising the DNA molecule of claim 1, 2, 3, or 4.

20. A method for producing a virus resistant plant cell comprising the steps of:

(a) making a DNA segment encoding a viral coat protein structural gene, wherein the coat protein encoded is that of a plant virus having a single-stranded tripartite RNA genome, and ligating the structural gene segment to a plant expressible promoter, the promoter being upstream from the structural gene such that a coat protein encoding RNA may be transcribed under the control of the promoter; and (b) transforming a transformable, regenerable plant cell to contain said DNA segment comprising said coat protein gene.

21. The method according to claim 20, wherein the coat protein encoded is that of a virus of the alfalfa mosaic virus group.

22. The method according to claim 21, wherein the virus of the alfalfa mosaic virus group is AMV.

23. The method according to claim 22, wherein the AMV is AMV strain 425.

24. A virus resistant plant prepared by the method of claim 10.

25. A virus resistant plant which is descended from the plant of claim 24.

* * * * *